(12) United States Patent
Spinler et al.

(10) Patent No.: US 6,415,649 B1
(45) Date of Patent: Jul. 9, 2002

(54) METHOD FOR LABORATORY MEASUREMENT OF CAPILLARY PRESSURE IN RESERVOIR ROCK

(75) Inventors: Eugene A. Spinler; Bernard A. Baldwin; David Mitchell Chancellor, all of Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/710,206

(22) Filed: Nov. 10, 2000

Related U.S. Application Data (62) Division of application No. 09/048,136, filed on Mar. 25, 1998, now Pat. No. 6,178,807.

(51) Int. Cl.[7] .............................. G01N 15/08; B04B 7/08
(52) U.S. Cl. ............................................. 73/38; 494/10
(58) Field of Search ................................ 73/38; 494/10, 494/85

(56) References Cited

U.S. PATENT DOCUMENTS

| | | | |
|---|---|---|---|
| 4,648,261 A | | 3/1987 | Thompson et al. ............ 73/38 |
| 4,728,892 A | | 3/1988 | Vinegar et al. ............. 324/309 |
| 4,868,500 A | | 9/1989 | Baldwin et al. ............. 324/307 |
| 5,079,948 A | | 1/1992 | Collins et al. ................. 73/153 |
| 5,245,859 A | | 9/1993 | Smith et al. .................... 73/38 |
| 5,328,440 A | * | 7/1994 | Chen et al. .................... 494/10 |
| 5,351,525 A | * | 10/1994 | Ragazzini et al. ............. 73/38 |
| 5,610,524 A | | 3/1997 | Longeron et al. ........... 324/376 |

* cited by examiner

*Primary Examiner*—Hezron Williams
*Assistant Examiner*—Michael Cygan
(74) *Attorney, Agent, or Firm*—Jeffrey R. Anderson (57) ABSTRACT

An effective laboratory method for developing complete capillary pressure curves involves directly measuring an oil/water saturation profile within a cylindrical porous rock core plug. The saturation profile, which includes a free water level, is established under a known pressure gradient induced by centrifuging and is measured using image mapping techniques. The free-water level is established at a desired position within the length of the core plug and provides a reference position of zero capillary pressure to facilitate measurement of both positive and negative capillary pressures.

5 Claims, 8 Drawing Sheets

METHOD FOR LABORATORY MEASUREMENT OF CAPILLARY PRESSURE IN RESERVOIR ROCK

This application is a division of application Ser. No. 09/048,136, filed Mar. 25, 1998, now U.S. Pat. No. 6,178,807.

The present invention relates to analysis of core samples of reservoir rock in a laboratory, and more particularly to a method for high precision measurement of fluid saturation as a function of applied pressure in the reservoir rock samples. In a still more specific aspect this invention relates to a method employing noninvasive imaging techniques to directly determine fluid saturation distribution as a function of distance inside a porous rock core plug, and using this saturation for deriving a complete set of capillary pressure curves.

BACKGROUND OF THE INVENTION

Knowledge of capillary pressure for each specific rock/oil/water combination present in reservoir rocks is highly important for predicting potential hydrocarbon recovery from the reservoir. Capillary pressure data, which is a measure of the interaction between fluids and the rock pore surface, includes determination of data that include development of complete positive and negative primary drainage, imbibition and secondary drainage curves. The strength of capillary interaction varies with the fluid saturations, the interfacial tension between the fluids, the pore structure, and the wettability of the pore surfaces. A measure of capillary pressure in a core sample can be calculated from the force exerted by the density difference between retained fluids at each height above or below a free water level in a centrifuged core. Knowing the fluid saturations as a function of the height above and below the free-water level permits the determination of a capillary pressure curve for any given reservoir rock/fluid system. Knowledge of the capillary pressure hysteresis, also called scanning curves, for a reservoir rock can be obtained in a laboratory. However, in practice this has been difficult to achieve, and is of uncertain accuracy or extremely time consuming to experimentally determine.

Capillary pressure curves are typically determined by either mercury intrusion, porous plate/membrane or centrifuge methods. Mercury intrusion, although rapid, provides questionable results due to the use of mercury in a vacuum to mimic water/oil behavior. Its methodology limits the technique to primary drainage and possible positive imbibition capillary pressures. Porous plate/membrane methods can generate all the capillary pressure curves, but to reach apparent equilibrium saturation can take days to months per pressure point for five to eight data points. This delays the availability of the results and limits the number of tests that can be made. The lengthy experimental time also increases the chance of a mechanical failure. The centrifuge method is normally used to determine drainage or negative imbibition curves. However, this method requires several centrifuge runs, which are time consuming such that it takes days to months to complete a test. A major limitation of the centrifuge methods is that it requires an assumed model to predict saturation distribution inside the core from the amount of liquid expelled. Accordingly, only an indirect or assumed or calculated measure of saturation at the inlet face of a rock plug is provided based on the amount of fluid expelled from the rock. Numerous methods over the past fifty years have been proposed for approximating the inlet saturation from centrifuge effluent volumes, but in every case, the model chosen influences the results, especially in the shape and location of the transition zone.

Accordingly, it is an object of this invention to derive complete positive and negative capillary pressure curves that closely mimic reservoir mechanism.

It is a more specific object of this invention to derive a capillary pressure curve that is determined from a measured oil/water saturation profile under a known pressure gradient as measured from a free-water level in a reservoir rock core sample.

A still more specific object is to establish an oil/water saturation distribution in a reservoir rock plug, via known fluid differential pressure by centrifuging.

Yet another object is to provide a method for deriving capillary pressure curves using noninvasive imaging techniques for determining fluid saturations, where the method is rapid, accurate and robust.

Still, another object of this invention is to provide methodology for capillary pressure measurement of rocks having a great disparity in petrophysical properties.

SUMMARY OF THE INVENTION

According to the present invention, the foregoing and other objects and advantages are attained by directly measuring an oil/water saturation profile within a porous rock core plug. The saturation profile, which includes a free water level, is established under a known pressure gradient induced by centrifuging, and is measured using image mapping techniques. The free water level is established at a desired position within the length of the core plug and provides a point of zero capillary pressure to facilitate measurement of both positive and negative capillary pressures.

In a preferred embodiment, oil and water saturation profiles within the rock plug are locked in place by freezing the oil phase while centrifuging, so that imaging the plug outside of the centrifuge allows direct mapping of the saturation profiles. In this manner both positive and negative portions of a capillary pressure curve are simultaneously obtained by calculating capillary pressure with reference to the free water level in the core plug as a point of zero capillary pressure. Complete capillary pressure curves are developed, which include a primary drainage curve of a core plug initially 100% saturated with water, a primary imbibition curve of a core plug initially at an irreducible water saturation, and a secondary drainage curve of a core plug initially at a residual oil saturation.

More specifically, the method for developing the primary drainage capillary pressure curve includes the following steps: fully saturating a generally cylindrically shaped core plug of porous rock with water, arranging the 100% water saturated core plug in a centrifuge holder and adding water and oil to the centrifuge holder so as to position a free water level encircling a cross section of the plug at a desired location along the length of the saturated core plug. Centrifuging the fully saturated core plug under oil and water for a predetermined length of time at a temperature above the melting point of the oil to establish the free water level within the plug, which then contains distributed water and oil. The core plug is cooled in the holder while still centrifuging to a temperature for solidifying the oil but not the water. Accordingly, distribution of fluids in the rock plug is fixed as the rock plug is removed from the centrifuge for imaging its saturation profile. Capillary pressure for each point of the saturation profile is then calculated from the force exerted on the retained fluid above and below the free water level for producing a primary capillary drainage curve for the core plug, which includes both positive and negative portions. Similar methods are used to obtain imbibition and secondary drainage capillary pressure curves, which each start with the core plug at an appropriate saturation state.

In another aspect, novel apparatus associated with the present invention includes a sample holder made of nylon for use in magnetic resonance imaging (MRI) or other noninvasive imaging devices. The holder, which is pressure sealed, is constructed to withstand high centrifugal forces encountered in a high speed centrifuge. The holder includes a sealable cup-like outer cylindrical member for holding an inner assembly. The inner assembly, which is used to centrally hold the core plug in the cup-like member, includes a circular bottom end piece, a circular top end piece, and three bar-like pieces which are longitudinally connected between the end pieces. The bar-like pieces have a width sufficient to provide a bulk annular volume between the core plug and outer cup-like structure of the holder that allows the core plug to be immersed in liquid while centrifuging.

The method and apparatus of this invention, is used to determine oil/water capillary pressure curves within a porous rock by establishing a freewater level in a core plug while centrifuging, and then freezing the oil phase while still centrifuging to facilitate saturation measurements on the core plug outside of the centrifuge. This method greatly reduces the time required to generate a set of capillary pressure curves including: equilibrium primary drainage, primary imbibition, and secondary drainage curves. Additionally, the method of this invention may reduce or eliminate many of the major limitations of other methods such as: determining the proper shape of capillary pressure curves; resolving questions on the impact of wettability/contact angle, saturation equilibrium, and boundary conditions. Further the method, which is applicable to diverse rock types, is accurate, rapid and robust.

Still other objects and advantages of the present invention will become readily apparent to those skilled in this art from the following detailed description, wherein there is shown and described only the preferred embodiment of the invention, simply by way of illustration of the best mode contemplated for carrying out the invention. As will be realized, the invention is suitable for other and different embodiments, and its several details are capable of modifications in various obvious respects, all without departing from the invention. Accordingly, the drawings and description are to be regarded as illustrative in nature, and not as restrictive.

DETAILED DESCRIPTION OF THE PREFERRED EMBODIMENT

A preferred embodiment of the invention as applied to a generally cylindrical core plug of reservoir rock will now be described, although it is to be understood that the invention is applicable to any porous media.

It is appropriate at this point to define several terms which are used in the following description and in the appended claims.

The term "core plug" refers to a cylindrical mass of porous material removed from a larger mass of the material.

The term "voxel" refers to a volume element in the sample of porous media being tested in accordance with this invention.

The term "pixel" refers to the smallest picture element that a device can display on-screen, and out of which the displayed image is constructed.

The term "saturation" is defined as the fraction (i.e. percent) of pore volume in the porous media which is filled with liquid. A sample that is 100% saturated has its' entire pore volume filled with liquid.

The "capillary pressure" at a particular point in a liquid containing sample of porous media, such as core plug of a reservoir rock, which is subjected to an acceleration alpha ($\alpha$) in a predetermined direction is expressed mathematically as a function $f(\alpha\rho, d)$, wherein $\rho$ is the liquid density difference and d is the distance measured from a free water level that is established at a point along the length of the plug.

Figure 1A:
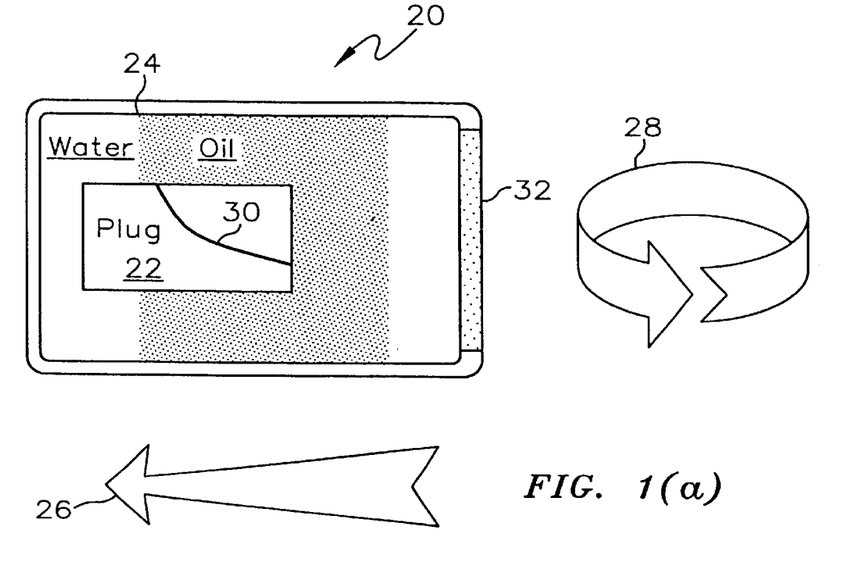
FIG. 1(a) is a schematic illustration for centrifuging a reservoir rock core plug with a free-water level in a large bulk volume centrifuge holder.
Figure 1B:
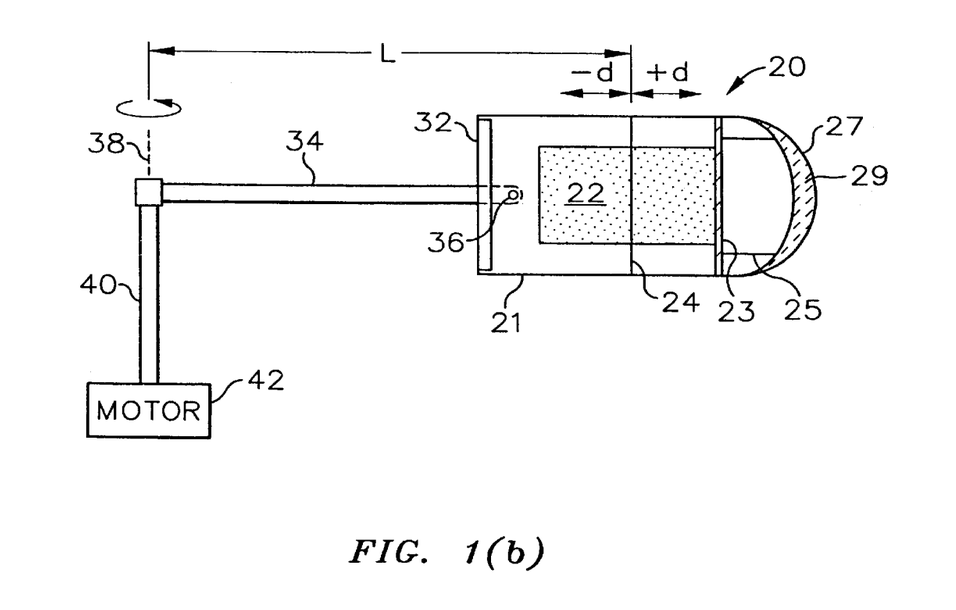
FIG. 1(b) is a simplified schematic illustration of a centrifuge apparatus.
Figure 1C:
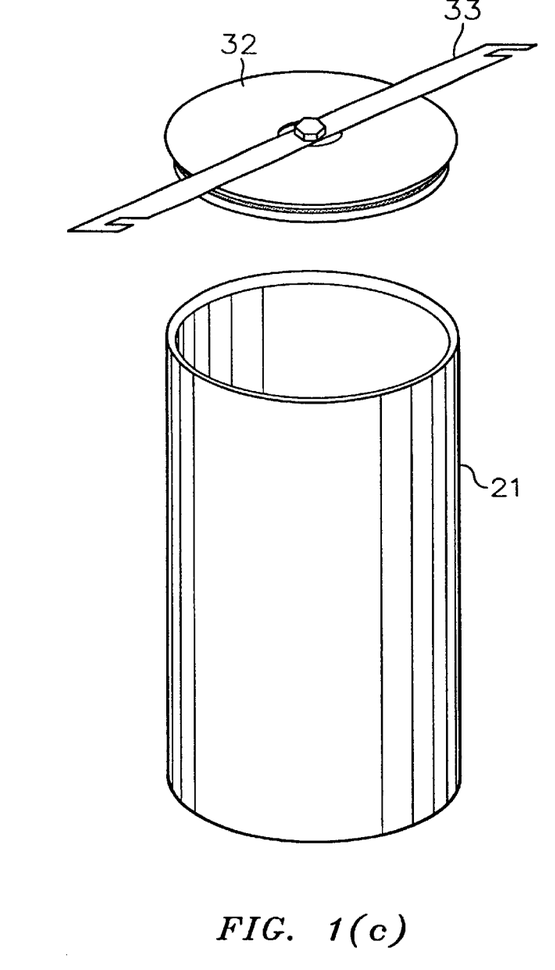
FIG. 1(c) is a perspective view of the cup member and lid of the centrifuge holder according to this invention.
Figure 1D:
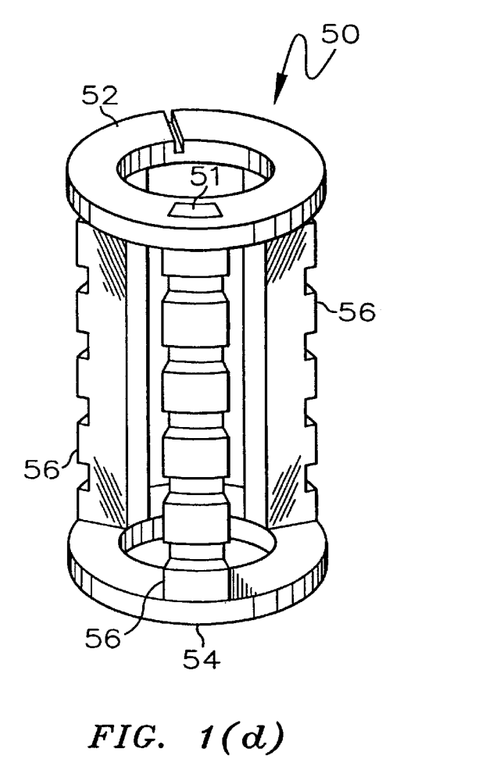
FIG. 1(d) is a perspective view of the core holder member of the centrifuge holder.
Figure 2:
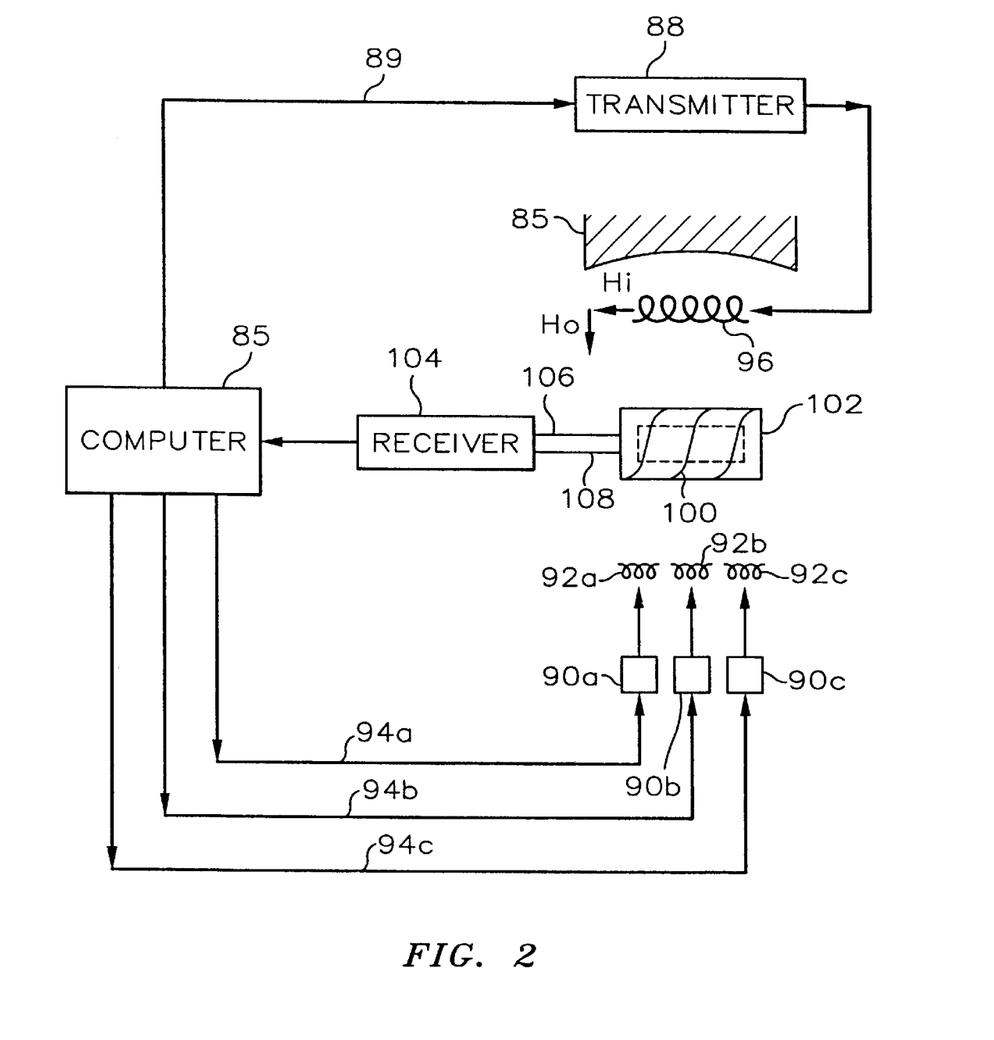
FIG. 2 is a schematic illustration of a magnetic resonance imaging (MRI) system.
Figure 3:
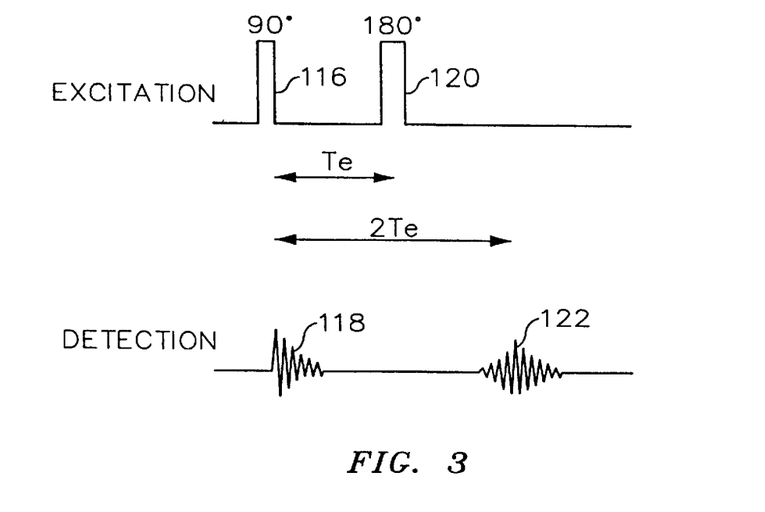
FIG. 3 illustrates a radio frequency pulse sequence and detected signals according to one embodiment of the invention.

The apparatus required for practicing the method of the present invention is illustrated in FIGS. 1, 2 and 3 and is briefly described below.

Referring now to FIG. 1(a), there is schematically illustrated the large bulk volume centrifuge sample holder, generally shown at 20. The holder 20, which contains a core plug 22, and a desired quantity of hydrocarbon oil and water so as to establish a free water level 24, is placed in a centrifuge with its axis in the direction of centrifugal force shown by the arrow at 26. While centrifuging, as indicated by the circular arrow 28, a capillary pressure curve develops in the porous rock plug as fluid saturation changes with the varying pressure induced by the centrifuge and the density difference between the oil and water. A typical primary drainage capillary pressure curve is illustrated at 30.

In FIG. 1(b), there is schematically shown a simplified centrifuge apparatus. A sample holder 20 includes a cup-like member 21 having a removable end closure 32. Also illustrated is a free water level 24, which is established prior to centrifuging. During centrifuging liquid flows from the core plug illustrated at 22, and another fluid is imbibed or injected and replaces the expelled fluid as it is expelled. As illustrated, the centrifugal sample holder is pivotally connected to swing arm 34 at a pivotal connection point 36 so that sample holder 20 assumes a generally horizontal position while centrifuging, and a vertical position when centrifuging stops. Swing arm 34 is driven about a rotational axis 38 by means of a drive shaft 40 and a motor 42. The cup-like member 21 contains an internal assembly, which is more fully described herein below. However, for simplicity the core plug 22 is shown in FIG. 1(b) as held against an apertured plate 23 by centrifugal force during centrifuging. A tubular member 25 is also illustrated between the plate 23 and the end 27 of the cup member 21. Accordingly, liquid flows during centrifuging from the core plug 22 and is collected as shown at 29.

The large bulk volume centrifugal sample holder 20, which may be employed in imaging apparatus such as MRI, X-ray scanning, X-ray attenuation or microwave system is better illustrated in FIGS. 1(c) and 1(d). More specifically, the preferred embodiment of the centrifugal holder has non-metallic or non-ferromagnetic structural members including an elongated tubular cup member 21 having a sealable lid 32 to form a fluid tight pressure assembly. A positioning bar for use with an MRI system is shown at 33. An interior assembly, generally shown at 50, which is also non-metallic or non-ferromagnetic, is provided for holding the core plug 22 and centering the plug 22 inside the cup 21. The interior assembly for the cup 21 preferably includes circular end pieces 52 and 54 permanently connected by three longitudinally extending bar members illustrated at 56. The bar members 56 are arranged so as to form an annular bulk volume between the cup 21 and the core plug 22 that is much larger than the volume of fluid inside the core plug. End member 52 has a bore therethrough for receiving the core plug 22, and one of the connecting members 56 has a bore 51 for receiving a standard sample material.

Referring now to FIG. 2 the primary elements of an MRI apparatus for use in the invention are schematically shown. The apparatus includes a resistive, permanent or superconducting, preferably superconducting, magnet 85 which produces a static magnetic field $H_o$ in the indicated direction. The apparatus further includes a computer 86 for controlling radio frequency (RF) transmitter 88 via signal line 89. The computer 86 also controls x, y and z gradient power supplies 90a, 90b and 90c and their corresponding gradient coils 92a, 92b and 92c via signal lines 94a, 94b and 94c, respectively. Transmitter 88 is adapted to produce radio frequency signals at a predetermined frequency which are received by RF coil 96 via line 98. RF coil 96 accordingly generates a radio frequency field $H_1$ in a direction perpendicular to $H_0$ and in a predetermined pulse sequence in response to commands from the suitably programmed computer 86. The gradient coils produce orthogonal gradient fields which are conventionally controlled by computer 86 so that predetermined voxels in the core plug being analyzed are "scanned."

Also as shown in FIG. 2, a receiver coil 100, comprising a suitable conductor such as copper tubing, is wound around a tubular member 102. Tubular member 102 is preferably composed of a material relatively transparent to radio frequency energy, such as Teflon® or polyethylene, and is sized to receive core plug 22 in its interior so as to conveniently position the core plug closely adjacent to and generally coaxial with the receiver coil 100. Of course, any means for suitably positioning core plug 22 with respect to receiver coil 100 is within the scope of the invention. It should also be understood that the relative positions of the receiver coil 100, magnet 85, RF coil 96 and gradient coils 92a, 92b and 92c are not necessarily as illustrated, but are rather depicted in FIG. 2 for ease of illustration.

The preferred MRI imaging system for saturation measurements is a Varian 85/310 CSI. This system has a 31 cm bore, a 2T superconducting magnet and operates at 85.55 MHz for hydrogen protons. A 9 cm ID saddle coil is used as both transmitting and receiving coil. The amount of fluid hydrogen protons is obtained using the Hahn spin-echo sequence with a 4 ms echo time and a 2.0 second recovery time. One slice, approximately 4 mm thick is obtained through the center axis of the plug. This orientation produces a rectangle which shows the saturation gradient aligned parallel to the centrifugal axis. The field of view is 9 cm×8 cm with a pixel resolution of 0.35×0.62 mm. A total of 16 repetitive measurements are averaged at each data point. The images consist of 255 levels of gray in a 256×256 display. The intensity of the individual pictures is adjusted to produce a presentable display, however, for quantitive determinations absolute intensities are used.

In a preferred embodiment of the method of the invention, a typical experiment for determining a primary drainage capillary pressure curve consists of selecting the rock sample, cutting it to the needed size, i.e., diameter and length for a core plug 22, cleaning the plug as necessary and saturating it with de-ionized water using known methods for saturating a porous rock such as "flash saturating." After saturating the core plug 22, the sides of the plug are sealed with a Teflon® sleeve to further constrain the direction of fluid flow to the axial direction, such that only the end faces of the core plug 22 are available for fluid to exit or enter. The free water level is established by centering the liquid water saturated core plug in the large bulk volume centrifuge holder cup 21 and adding desired amounts of de-ionized water and a hydrocarbon oil such as high purity octadecane in the annular volume surrounding the plug. The position of the final oil water contact is adjusted by adding appropriate amounts of each fluid. This adjustment is approximate since one fluid is expelled from the core plug 22 while centrifuging and the other fluid enters the core plug 22. This approximation is minimized, however, by making the bulk volume surrounding the core plug significantly greater than the volume of fluid inside the core plug. The cup-like member 21, which contains the saturated core plug, oil and water, is sealed using the lid 32 and then is placed in the centrifuge with its axis in the direction of centrifugal force as illustrated in FIG. 1(a). Centrifuging is carried out at a predetermined speed, typically in the range of about 500 to about 5,000 RPM, using a centrifuge having both heating and cooling means. Suitable centrifuges include: a Beckman L5-50 p using a horizontal head, and a Sorvl RC 26 plus with a swinging bucket. Another centrifuge, which is used to obtain calibration data, is a Sorvall ultracentrifuge OTD65B with a TI 45 angle head. Centrifuging is carried out for such a time until a state of equilibrium is reached where fluid flow in the core plug terminates. The time needed for centrifuging depends on how rapidly the fluids reach their equilibrium saturation in the centrifuge, and is largely determined by the permeability of the rock and viscosity of the fluids. The majority of fluid distributions for reservoir rocks can be obtained in a few hours, however, as the relative permeability of the minor fluid decreases with decreasing saturation rate, the saturation rate will decrease significantly, especially for low permeability rocks such as chalk. This means that some rocks may be in the centrifuge at a stable speed for an extended period of time. Typical centrifuge times, however, range from about one hour to about eight hours.

To obtain the oil/water saturation profile that exists while centrifuging, the preferred method is to freeze only the oil phase while centrifuging, and map the water saturation in the rock via magnetic resonance imaging (MRI) techniques outside of the centrifuge. Other imaging methods are also applicable, however, MRI is preferred for convenience and high spatial resolution. Freezing the hydrocarbon oil but not the water while centrifuging prevents redistribution of the water in the rock when it is removed from the centrifuge. In a solid state, the MRI relaxation time of the hydrocarbon oil is so short that it does not image. Thus, in this experiment the water is imaged and octadecane, which freezes at twenty-seven degrees Celsius, is not imaged. Laboratory ambient temperature is typically about twenty-three degrees Celsius, and accordingly little risk is present for melting the oil phase and allowing fluid movement outside of the centrifuge.

After the oil phase in the plug is frozen in the centrifuge, the sealed sample holder for the plug is removed from the centrifuge and transferred to MRI system for saturation distribution measurement. The core plug 22 is kept in the sealed container during handling and imaging to prevent evaporation of the water. Referring again to FIG. 2, for MRI imaging the core plug 22 it is subjected to the static magnetic field, $H_o$ as produced by the magnet 85. Spinning hydrogen nuclei of the liquid act as magnetic dipoles which are caused to align with the static magnetic field such that magnetization vectors associated with the spinning nuclei precess a certain precessional frequency around axes which are parallel to the direction of the static field.

The core plug 22 is then subjected to a radio frequency field $H_1$ as generated by RF coil 96. The frequency selected must be the resonant frequency, that is the RF field must be equivalent to the precessional frequency of the spinning nuclei so as to achieve resonance. Generally, the radio frequency field is applied to the core plug as a pulse or sequence of pulses only a few milliseconds in duration. The presently preferred pulse sequence is known as the Hahn spin echo sequence which is illustrated in FIG.3.

Referring now specifically to FIG. 3, a pulse 116 is applied of sufficient amplitude and duration to cause the precessional axes of the precessing nuclei to rotate 90 degrees to a nonequilibrium, excited state which causes a voltage to be induced in the receiver coil. The resulting signal is shown at 118, which is sometimes called an FID (free induction delay) signal. At a time "spin echo time" Te, typically about one to about sixty milliseconds, after pulse 116, a second pulse 120 is applied of sufficient amplitude and duration to cause the precessional axes to rotate another 180 degrees to a nonequilibrium state which causes the production of a single "spin echo" signal 122 at a time Te after application of the second pulse. The duration of Te is primarily dependent on pore size. Generally, smaller pore sizes require shorter Te values. The spin echo signal shown corresponds to a single voxel in the core plug. The plug is scanned using the gradient coils in a conventional manner to obtain spin echo signals corresponding to other voxels in the core plug. It is preferable and most convenient, as should become apparent below, to utilize a planar scanning technique, well known to those skilled in the art, whereby a plurality of signals are obtained corresponding to a "slice" of voxels which lie along a plane. Preferably this slice lies along the longitudinal axis of the plug. Referring back to FIG. 2 the signals are presented to computer 86 for processing. The amplitude of each of the spin echo signals is stored in the computer as intensity values that are assembled to map the water distribution in the core plug.

Although the pulse sequence described above is preferred due at least in part to its relative ease of implementation, other pulse sequences which produce at least one MRI signal for a corresponding voxel are within the scope of the invention. For example only a single 90 degree pulse can be applied resulting in the FID signal. The FID signals for a plurality of voxels can be stored in the computer in a manner similar to that discussed with respect to the spin echo signals. Another alternative is the Carr-Purcell pulse sequence which involves a 90 degree pulse, followed by several 180 degree pulses and then another 90 degree pulse. Regardless of the pulse sequence used and resulting MRI signals, the amplitude of such signals and representative intensities can be easily related to saturation in a manner described below.

Figure 4:
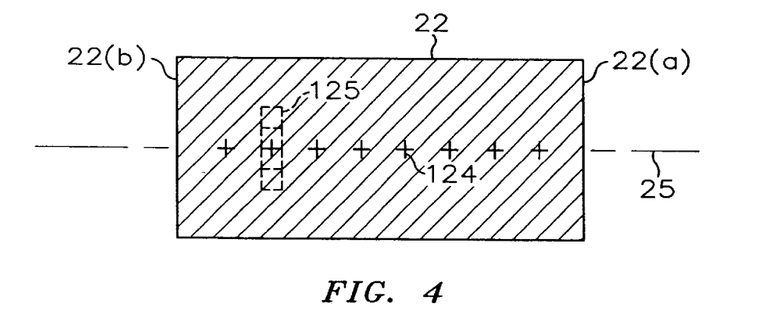
FIG. 4 shows a core plug in section with locations of interest represented by crosses, and voxels corresponding to a particular location represented by dashed lines.

Referring now to FIG. 4, the core plug 22 is shown with a plurality of selected locations at 124 represented by crosses. Locations 124 are selected for the determination of corresponding saturation and capillary pressure values. Several voxels 125 associated with a particular location 124 are also shown. Of course, only two dimensions are illustrated, whereas the voxels are three dimensional. Moreover, the illustrated voxels, whose sides are typically only a fraction of a millimeter in length, are not shown to scale for clarity of illustration.

Locations 124 are shown as lying along axis 25 of the core plug 22, although these selected locations could lie along a line parallel to but offset from the longitudinal axis. Other spatial arrangements for the selected locations are also within the scope of the invention, as long as the locations are spaced a plurality of different distances from end 22a, wherein distance is measured along lines parallel to the axis 25. It will become apparent that by selecting locations spaced different distances from end 22a, the locations will have different capillary pressures associated therewith which are employed in a manner discussed in detail hereinafter to obtain a capillary pressure curve. The use of locations along the axis as illustrated is preferred in accordance with the invention and has been found to give most accurate results.

An MRI intensity value corresponding to each location 124 is preferably determined by averaging the MRI intensity values for a number of adjacent voxels. For example the MRI intensity value for a particular location 124 as shown in FIG. 4 is determined by averaging the individual intensity values corresponding to several voxels, as shown at 125.

Only four voxels are shown in FIG. 4, however, a greater number of voxels are contemplated, which define a cluster centered around the particular location of interest.

Figure 5A:
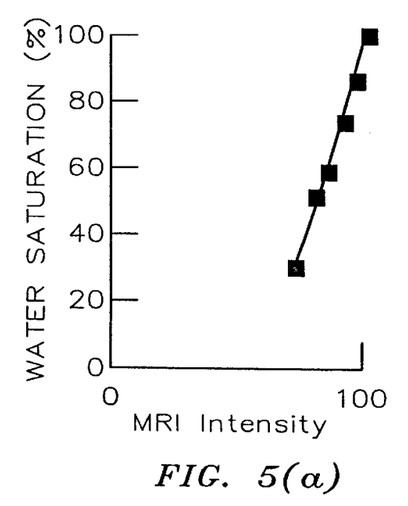
FIG. 5(a) is a calibration curve from an air-water porous plate desaturation showing MRI intensity versus percent water saturation for a sandstone core plug.
Figure 5B:
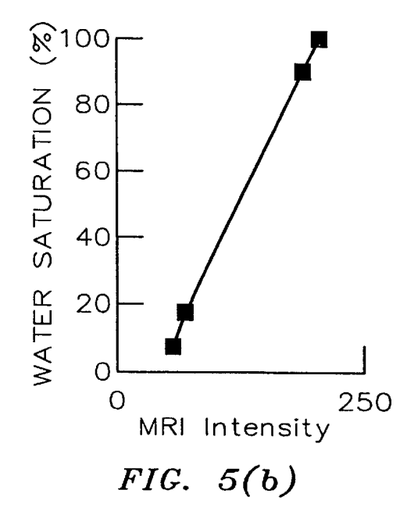
FIG. 5(b) is a calibration curve similar to FIG. 5(a) showing MRI intensity versus percent water saturation for a chalk core plug.

The MRI intensity map of the water distribution is directly converted to water saturation via calibration curves. The small volume change (approximately 2%) created by the hydrocarbon contraction during freezing is corrected by adjusting the water saturation. Calibration curves are measured for air-water images of the core plugs at varying water saturation states. Once a relatively uniform saturation state in a plug is obtained, average MRI intensity is cross-plotted with average water saturation obtained by weight measurements using a large diameter porous disk for desaturation. These calibration curves, which are used to determine percent saturation, are illustrated in FIG. 5(a) for a Berea sandstone rock plug, and in FIG. 5(b) for a chalk plug.

Capillary pressure as a function of position in the core plug 22 and the achievable pressure range is determined by the speed of the centrifuge, the distance from the free water level, and the length of the core plug. Positioning the free water level along the length of the core plug establishes a position of zero capillary pressure in the mid-section of the plug, and thus enables development of both the positive and negative portions of a capillary pressure scanning curve simultaneously. The free-water level is imaged with the plug so as to enable an accurate calculation of capillary pressures in the plug without questions regarding the boundary conditions at the end of the plug, as is common to other centrifuge methods. The imaging technique also enables nonuniform boundary conditions such as radial artifacts to be visually assessed and avoided or corrected.

Referring again to FIG. 1(b), capillary pressure for each location of the core plug 22 is calculated using the basic expression $\rho \alpha d$, where $\rho$ is the density of the liquid, $\alpha$ is the acceleration to which the core plug is subjected during centrifuging, and d is the distance as measured parallel to the core longitudinal axis from the free water level to the location of interest. The acceleration can be expressed in terms of the angular velocity $\omega$ of the core plug during centrifuging, the distance L measured between the rotational axis and the free water level 24, and the distance d measured from the free water level to the point of interest to give the following expression for capillary pressure P:

$$P=\rho[(L+d)\omega^2]d$$

The capillary pressure can be expressed in, for example, psi, dynes/cm², or newtons/m². If expressed in dynes/cm², $\rho$ is in grams/cm³, L and d are in cm, and $\omega$ is in radians/second. Another, and more convenient expression for capillary pressure P in psi, in terms of density $\rho$ in gram/cm³ and L and d in cm, can be derived from the above equation by expressing $\omega$ in terms of centrifuging speed RPM (i.e. $\omega=2\pi RPM/60$) and applying a conversion factor to convert dynes/cm² to psi. Such an expression is given below:

$$P=(1.5908\times10^{-7})\rho(L+d)(RPM)^2 d$$

It is noted that acceleration due to gravitational force is generally so minute as compared to alpha that no correction is needed in this regard.

Accordingly, from the above described determinations of percent saturation and capillary pressure a capillary pressure curve is plotted. The preparation of the core plugs and the sequencing of the centrifuge steps is important in control of the direction of fluid flow so as to observe possible hysteresis effects. The following simplified generalized chronological sequence is used to produce complete positive and negative capillary pressure scanning curves:

1) Prepare the plug to 100% saturation of the wetting fluid.
2) Centrifuge with a free water level contacting the plug to produce the primary drainage capillary pressure curve.
3) Invert and centrifuge the plug from step two in the non-wetting fluid. Repeat and invert the plug again to reach a relatively uniform saturation distribution throughout the plug at an irreducible water saturation to prepare the plug for imbibition.
4) Centrifige the plug from step three with a free water level in contact with the plug. The free water level is adjusted to achieve the range of positive and negative capillary pressure curves desired for producing a primary imbibition capillary pressure curve.
5) Invert and centrifuge the plug from step four in the wetting fluid. Invert the plug and repeat to reach a relatively uniform saturation distribution throughout the plug at residual oil saturation to prepare the plug for secondary drainage.
6) Centrifuge the plug from step five with a free water level contacting the plug. The free water level is adjusted to achieve the range of positive and negative curves desired for producing the secondary drainage curve.
7) Steps three to six may be repeated to evaluate additional hysteresis effects for the capillary pressure curves.

Capillary pressure measurements of two diverse rock types, i.e., Berea sandstone and reservoir chalk, were made according to the above-described preferred method of the invention. Table I below shows petrophysical properties and dimensions of the core plugs.

TABLE I

Reservoir Rock Core Plugs

| Type | Length (cm) | Diameter (cm) | Porosity (percent) | Permeability (md) |
|---|---|---|---|---|
| Berea | 4.78 | 2.54 | 0.20 | 612 |
| chalk | 3.94 | 2.54 | 0.33 | 5 |

Figure 6A:
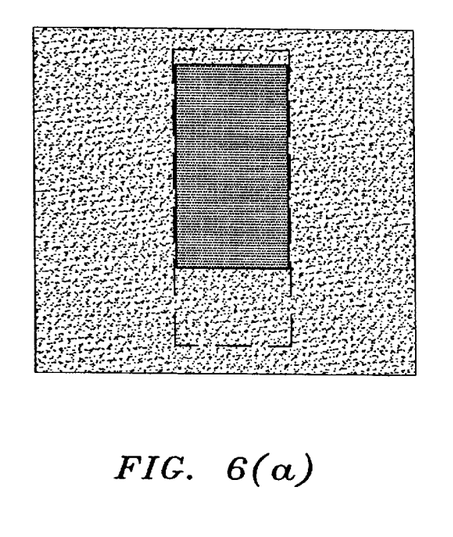
FIG. 6(a) is an image of a Berea sandstone plug at 100% saturation where the dashed rectangle encloses the imaged area.
Figure 6B:
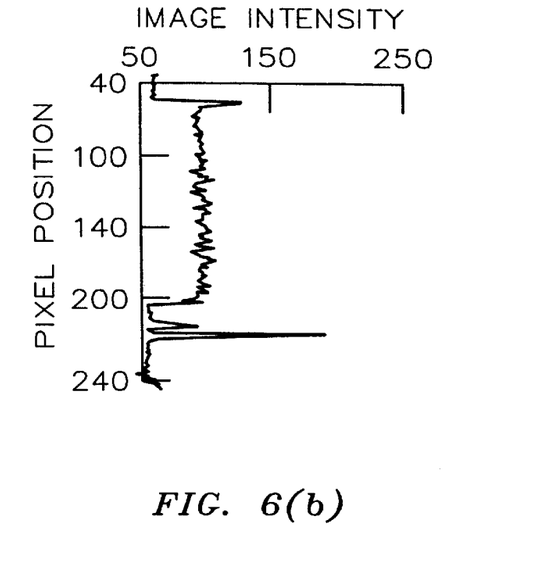
FIG. 6(b) is the MRI intensity map for the area of the Berea sandstone plug enclosed in the dashed lines of FIG. 6(a).
Figure 7A:
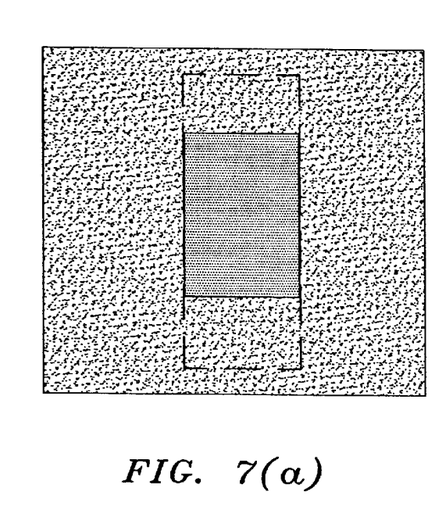
FIG. 7(a) is an image similar to FIG. 6(a) for a chalk plug.
Figure 7B:
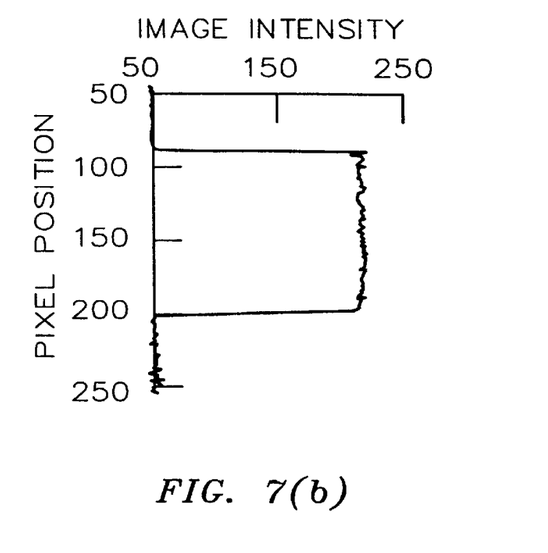
FIG. 7(b) is an MRI intensity map similar to FIG. 6(b) for a chalk plug.

Images of the 100% water saturated core plugs and a corresponding intensity map for each of the plugs is shown in FIGS. 6 and 7. Each of the intensity maps, shown in FIG. 6(b) for the Berea plug and in FIG. 7(b) for the chalk plug were constructed from the image area bounded by the dashed rectangle in the corresponding FIGS. 6(a) and 7(a). All profiles, which represent the average intensity along the length of the plug, are averaged measurements which are averaged across the core perpendicular to the centrifugal axis. These measurements include 133 averaged measurement for the Berea (FIG. 6(b)) sandstone plug, and 105 averaged measurements for the chalk plug. The larger random variations in the intensity map for the Berea sandstone reflects the less uniform porosity found in the sandstone as compared to the chalk, and does not represent a higher noise level.

Figure 8A:
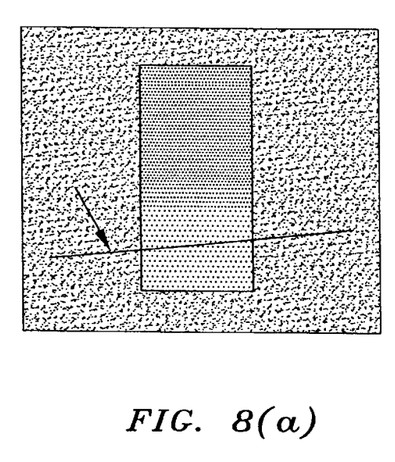
FIG. 8(a) is an MRI image of a Berea sandstone plug at primary drainage where the arrow indicates marked free water level.

An image of the Berea plug with a primary drainage saturation distribution is shown in FIG. 8(a). The image includes a reference standard to its left, and is imaged with free water, which is the bright area near the bottom of the plug. An arrow indicates a line where the free water level was located along the plug. Dark areas represent either solid octadecane or the sample core plug holder. Although, this plug was desaturated using a swinging bucket at 1500 rpm, the free water level was not vertical, probably due to gravity. The impact of this sloping free water level was considered in the calculation of capillary pressures and would play an increasing role only at lower centrifuge speeds. Since the image was obtained as a four mm slice parallel to the centrifuge axis, radial effects can be neglected.

Figure 8B:
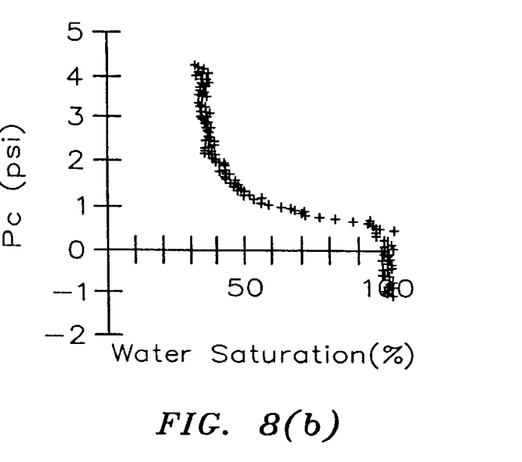
FIG. 8(b) is a primary drainage capillary pressure curve ($P_c$) for the Berea plug imaged in FIG. 8(a)

The primary drainage capillary pressure data corresponding to FIG. 8(a) are shown in FIG. 8(b). Some scatter in the data results from porosity variations in the plug, but a capillary pressure curve could be easily drawn through the data over the seven pound pressure range.

Figure 8C:
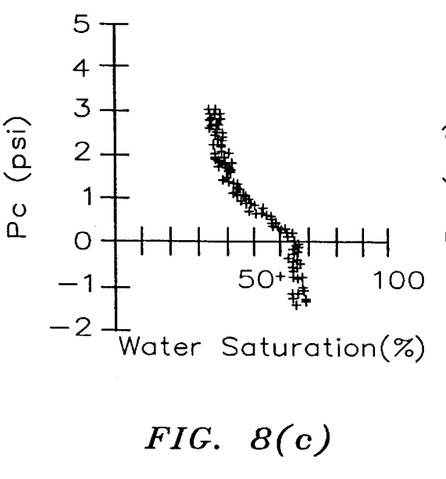
FIG. 8(c) is an imbibition curve for the Berea sandstone plug.

The imbibition capillary pressure data for the Berea plug are shown in FIG. 8(c). Positive and negative data were obtained by placing the free water level near the center of the plug. The data crosses the free water level ($P_c=0$) at $S_w$ equal to 62 percent and forms the basis for a bounding capillary pressure curve.

Figure 8D:
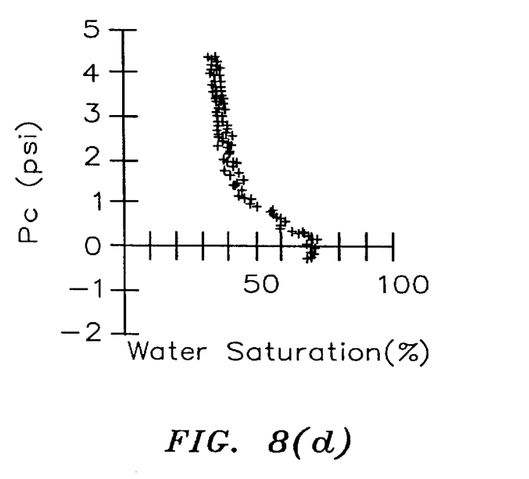
FIG. 8(d) is a secondary drainage curve for the Berea sandstone plug.

The secondary drainage capillary pressure data for the Berea plug are shown in FIG. 8(d). The free water level was placed near the outlet end of the plug. The secondary drainage data form the basis for the upper bounding capillary pressure curve.

Figure 9A:
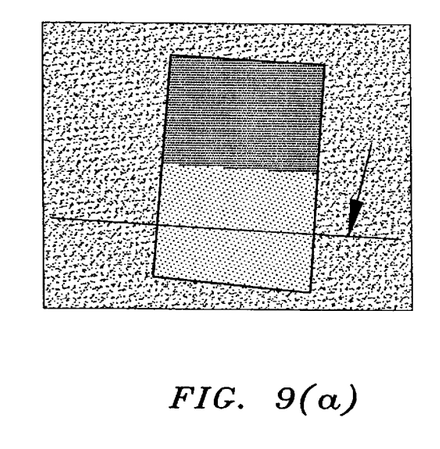
FIG. 9(a) is an MRI image of a chalk plug at primary drainage, where the arrow indicates a marked free water level.

An image of the chalk plug with a primary drainage saturation distribution is shown in FIG. 9(a). The free water was removed prior to imaging and only residual water remains on the boundary. An arrow indicates a line where the free water level was along the plug. This plug was desaturated using a horizontal centrifuge head at 7000 rpm. The free water level was close to vertical and no adjustments were made for gravity. The tilt to the image merely reflects that the plug was not parallel to the axis of the MRI when imaged. Since the image was obtained as a 4 mm slice parallel to the centrifuge axis, radial effects were neglected.

Figure 9B:
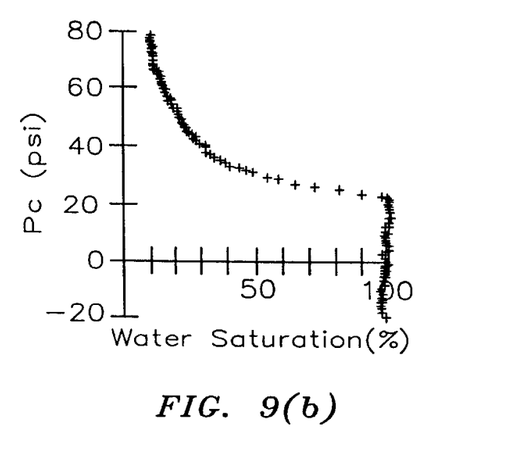
FIG. 9(b) is a primary drainage capillary pressure curve ($P_c$) for the chalk plug imaged in FIG. 9(a).

The primary drainage capillary pressure data corresponding to FIG. 9(a) are shown in FIG. 9(b). There is little scatter in the data since the porosity variations in the plug were small. A capillary pressure curve could be easily drawn through the data over the one-hundred pound pressure range.

Figure 9C:
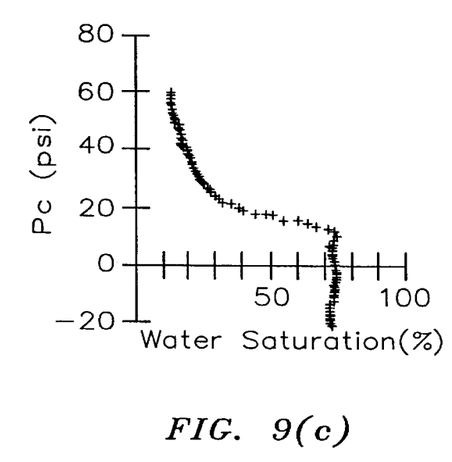
FIG. 9(c) is an imbibition curve for the chalk plug.

The imbibition capillary pressure data for the chalk plug are shown in FIG. 9(c). Positive and negative data were obtained by placing the free water level along the side of the plug. The data cross the free water level ($P_c=0$) and $S_w$ equal to 72 percent and forms the basis for a bounding scanning capillary pressure curve.

Figure 9D:
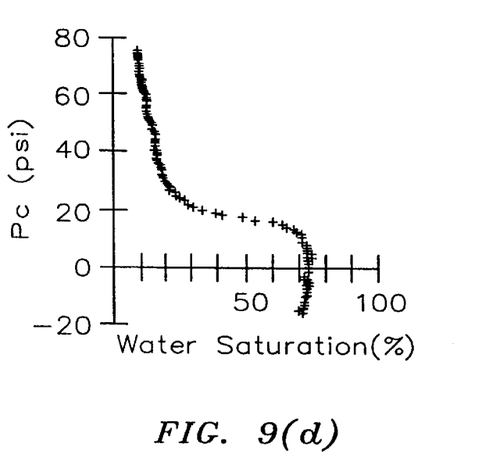
FIG. 9(d) is a secondary drainage curve for the chalk plug.

The secondary drainage capillary pressure data for the chalk plug are shown in FIG. 9(d). The crosslinking point for secondary drainage was at $S_w$ equal to 72 percent confirming that the plug was highly water-wet. The secondary drainage data form the basis for the upper bounding capillary pressure curve.

Figure 10:
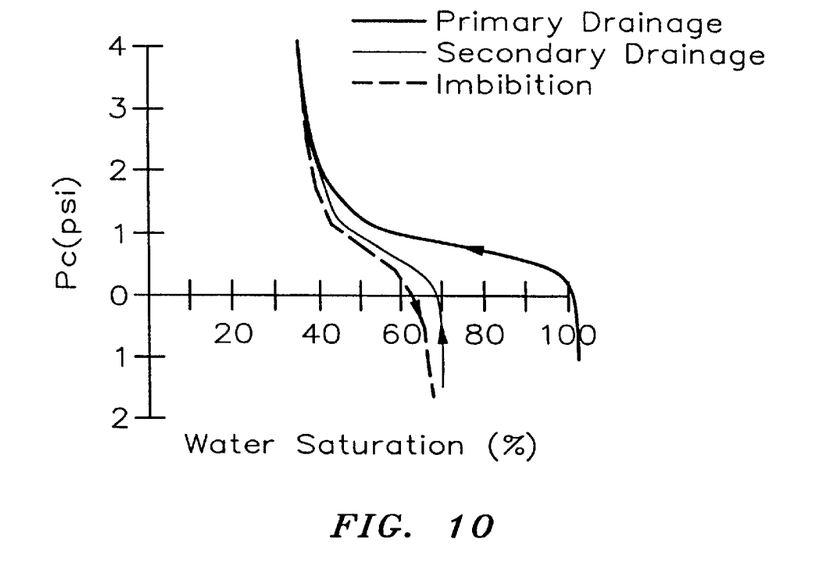
FIG. 10 illustrates smoothed capillary pressure curves for the Berea plug showing details of the bounding curves.
Figure 11:
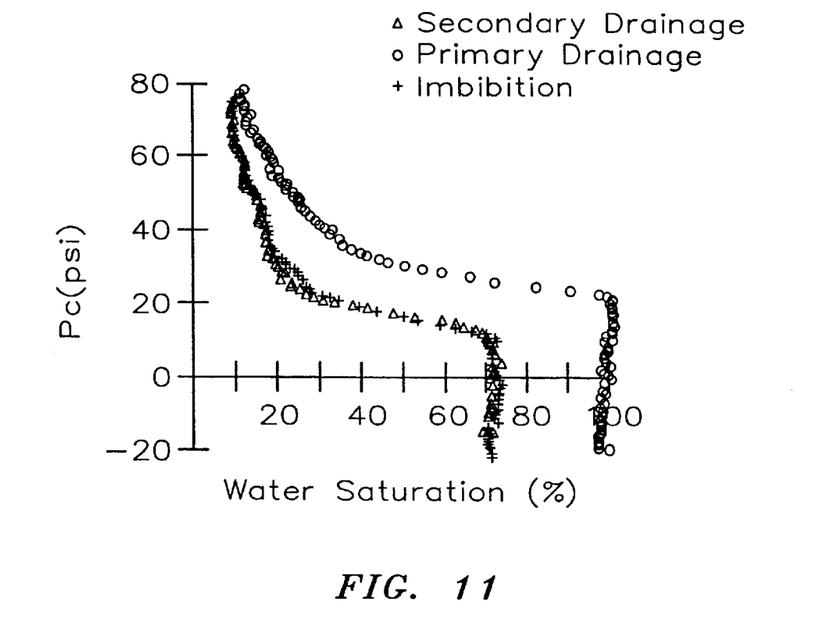
FIG. 11 illustrates actual capillary pressure curves of the chalk plug showing no hysteresis of the bounding curves.

Overlays of the scanning curves for Berea and chalk plugs are shown in FIGS. 10 and 11 respectively. The Berea data have been smoothed and it is apparent that closure to bounding curves was not obtained. By placing the free water level to obtain more of the negative portion of the $P_c$ curve, it should be possible to achieve closure. No smoothing was applied to the chalk data, and it can be seen that the imbibition and secondary drainage curves overlay. The more uniform porosity distribution in chalk and a high degree of connectivity between pores (high coordination number) may account for the lack of hysteresis between the imbibition and secondary drainage curves for the chalk.

The time needed to complete each step of the above test depended on how rapidly the fluids reached their equilibrium saturation in the centrifuge, and was largely determined by the permeability of the rock. This was especially true for low permeability chalk which had to be centrifuged up to twelve days to obtain and verify a single stabilized saturation profile compared to two days for the Berea sandstone. Once a calibration curve is available, the total experimental time to generate a set of equilibrium primary drainage, primary imbibition and secondary capillary pressure curves would take approximately sixteen days for a Berea sandstone plug and approximately 1.5 months for a low permeability chalk plug. However, with a centrifuge head capable of holding more than one plug, the average time for three to four plugs could be similar to that for one plug.

The invention as described and illustrated herein is an effective method and apparatus for rapidly developing complete set of capillary pressure curves, wherein placing the free water level along the length of rock plugs; freezing the oil phase during centrifuging; and direct measurement of saturation by NMRI techniques provides an accurate, rapid and robust laboratory method for determining capillary pressure scanning curves in a porous media. However, those skilled in the art of core plug analysis will recognize that many modifications and variations of the present invention are possible in light of the above teachings without departing from the spirit of the invention. It is to be understood that although the invention has been described mainly in the context of studies involving porous oil bearing rock formations in which de-ionized water is the fluid used to drive oil from the pores, the invention may be carried out using various other fluids such as brine or deuterium oxide for the wetting phase. Likewise, various oils such as pentadecane, nonadecane, or crude oil, which remain frozen at ordinary room temperatures, may be employed in the invention. It should also be understood that changes to other features or aspects that do not affect the overall basic function and concept of the invention may be made by those skilled in the art without departing from the spirit and scope of the invention, as defined by the appended claims.

That which is claimed is:

1. A centrifuge holder for a core plug of porous rock adapted to allow immersion of said core plug in at least one liquid, said centrifuge holder comprising:
   (a) an outer enclosure comprising:
      i) an elongated tubular member having an opening at one end permanently sealed to form a cup-like member;
      ii) a lid for sealingly closing the opening of said cup-like member;
   (b) an interior assembly for holding said core plug, wherein said interior assembly containing said core plug is adapted for disposal within said cup-like member, said interior assembly comprising:
      i) a first flat disc shaped end member;
      ii) a second end member shaped as a flat annular ring having a circular opening adapted for closely receiving said core plugs; and
      iii) a plurality of bar-shaped connecting members, each of which is lengthwise connected at evenly spaced intervals between said first and second end members, and wherein an outer edge of each of said plurality of connecting members is positioned adjacent the periphery of said first and second end members, and an inner edge of each of said connecting members is positioned adjacent the periphery of said annular opening in said second end member for containing said core plug; and
   (c) wherein the bulk volume of empty space in said outer enclosure when containing said core plug is much greater than the volume of liquid contained in said core plug, and is sufficient to allow immersion of said core plug in liquid.

2. A centrifuge core holder in accordance with claim 1, wherein said outer enclosure and said interior assembly are constructed of non-metallic and non-ferromagnetic material.

3. A centrifuge core holder in accordance with claim 1, wherein said centrifuge core holder is pressure sealed.

4. A centrifuge holder in accordance with claim 1, wherein said core plug is immersed in two immiscible liquids comprising hydrocarbon oil and water to establish a free-water level along the length of said core plug.

5. A centrifuge holder for a core plug of porous rock adapted to allow immersion of said core plug in at least one liquid, said centrifuge holder comprising:
 (a) an outer enclosure comprising:
  i) an elongated tubular member having an opening at one end permanently sealed to form a cup-like member;
  ii) a lid for sealingly closing the opening of said cup-like member;
 (b) an interior assembly for holding said core plug, wherein said interior assembly containing said core plug is adapted for disposal within said cup-like member, said interior assembly comprising:
  i) a first flat disc shaped end member;
  ii) a second end member shaped as a flat annular ring having a circular opening adapted for closely receiving said core plugs; and
  iii) a plurality of bar-shaped connecting members, each of which is lengthwise connected at evenly spaced intervals between said first and second end members, and wherein an outer edge of each of said plurality of connecting members is positioned adjacent the periphery of said first and second end members, and an inner edge of each of said connecting members is positioned adjacent the periphery of said annular opening in said second end member for containing said core plug;
 (c) wherein the bulk volume of empty space in said outer enclosure when containing said core plug is much greater than the volume of liquid contained in said core plug, and is sufficient to allow immersion of said core plug in liquid; and
 wherein said core plug is immersed in two immiscible liquids comprising hydrocarbon oil and deuterium oxide.

* * * * *